United States Patent
Goenka et al.

(10) Patent No.: US 10,866,202 B2
(45) Date of Patent: Dec. 15, 2020

(54) TEXTILE ARTICLES AND SYSTEMS FOR LIQUID DETECTION

(71) Applicant: Welspun India Limited, Mumbai (IN)

(72) Inventors: Dipali Goenka, Mumbai (IN); Mili Tharakan, Mumbai (IN); Apurv Kodgule, Mumbai (IN); Rajender Sharma, Mumbai (IN)

(73) Assignee: Welspun India Limited, Mumbai (IN)

( * ) Notice: Subject to any disclaimer, the term of this patent is extended or adjusted under 35 U.S.C. 154(b) by 0 days.

(21) Appl. No.: 16/134,454

(22) Filed: Sep. 18, 2018

(65) Prior Publication Data

US 2019/0017951 A1 Jan. 17, 2019

Related U.S. Application Data

(63) Continuation of application No. 15/275,191, filed on Sep. 23, 2016, now Pat. No. 10,101,289.

(Continued)

(51) Int. Cl.
*G01N 27/04* (2006.01)
*A61B 5/00* (2006.01)
(Continued)

(52) U.S. Cl.
CPC ......... *G01N 27/048* (2013.01); *A47C 27/007* (2013.01); *A47C 31/00* (2013.01); *A47G 9/00* (2013.01); *A61B 5/02042* (2013.01); *A61B 5/6801* (2013.01); *A61B 5/6892* (2013.01); *A61F 13/42* (2013.01); *D02G 3/441* (2013.01); *D04B 1/14* (2013.01); *D06P 5/30* (2013.01);

(Continued)

(58) Field of Classification Search
CPC .. G01N 27/048; G01N 27/121; G01N 27/223; A61F 13/42; A61F 2013/428; A01G 25/167
USPC ........................................................ 324/694
See application file for complete search history.

(56) References Cited

U.S. PATENT DOCUMENTS 3,778,570 A * 12/1973 Shuman .................... A61F 5/48
200/61.05
5,291,181 A * 3/1994 DePonte ................. A61F 13/42
128/886

(Continued)

FOREIGN PATENT DOCUMENTS

DE 202014103821 U1 9/2014
WO 2005093397 A1 10/2005
WO 2006089377 A1 8/2006

OTHER PUBLICATIONS

Parkova et al., Design of Textile Moisture Sensor for Enuresis Alarm System, Material Science, Textile and Clothing Technology, 2012, pp. 44-49.

(Continued)

*Primary Examiner* — Christopher P McAndrew
(74) *Attorney, Agent, or Firm* — Offit Kurman, P.A.; Gregory A. Grissett

(57) ABSTRACT

Systems and methods are provided for detecting liquid in a textile article using one or more flexible sensors integrated in the textile article. The sensor data is forwarded to a computing device via a communication link by an interface element associated with the textile article. The computing device detects a location of liquid in the textile article proximate to the one or more flexible sensors based on a determination that a criterion is met.

15 Claims, 10 Drawing Sheets

Related U.S. Application Data

(60) Provisional application No. 62/232,443, filed on Sep. 25, 2015.

(51) Int. Cl.

| | | |
|---|---|---|
| *A61F 13/42* | (2006.01) | |
| *A61B 5/02* | (2006.01) | |
| *A47C 27/00* | (2006.01) | |
| *A47C 31/00* | (2006.01) | |
| *A47G 9/00* | (2006.01) | |
| *A61F 13/15* | (2006.01) | |
| *D02G 3/44* | (2006.01) | |
| *D06P 5/30* | (2006.01) | |
| *D04B 1/14* | (2006.01) | |
| *H05K 3/12* | (2006.01) | |
| *D06M 23/16* | (2006.01) | |

(52) U.S. Cl.
CPC ............. *A61B 2562/029* (2013.01); *A61F 2013/15056* (2013.01); *A61F 2013/424* (2013.01); *D06M 23/16* (2013.01); *D10B 2401/18* (2013.01); *H05K 3/12* (2013.01); *H05K 2201/10151* (2013.01)

(56) References Cited

U.S. PATENT DOCUMENTS

| | | | | |
|---|---|---|---|---|
| 5,459,452 A * | 10/1995 | DePonte | A61F 13/42 | 128/886 |
| 5,796,345 A * | 8/1998 | Leventis | A61F 13/42 | 340/604 |
| 5,866,801 A * | 2/1999 | Johnson | G01N 15/08 | 73/38 |
| 5,903,222 A | 5/1999 | Kawarizadeh et al. | | |
| 5,950,264 A * | 9/1999 | Wyner | A47C 27/006 | 5/490 |
| 6,315,009 B1 | 11/2001 | Jayaraman et al. | | |
| 6,499,338 B2 * | 12/2002 | Li | G01N 27/048 | 19/66 R |
| 6,583,722 B2 * | 6/2003 | Jeutter | A61F 13/42 | 340/573.1 |
| 6,603,403 B2 * | 8/2003 | Jeutter | G06K 19/0716 | 340/604 |
| 6,687,523 B1 | 2/2004 | Jayaraman et al. | | |
| 6,970,731 B1 * | 11/2005 | Jayaraman | A61B 5/0008 | 600/388 |
| 7,594,442 B2 * | 9/2009 | Kaiserman | B60N 2/002 | 73/760 |
| 8,171,755 B2 | 5/2012 | Jahn et al. | | |
| 8,383,875 B2 * | 2/2013 | Long | A61F 13/42 | 604/361 |
| 8,750,959 B2 | 6/2014 | Lindberg et al. | | |
| 8,826,473 B2 * | 9/2014 | Flanagan | G08B 21/20 | 5/600 |
| 8,884,769 B2 * | 11/2014 | Novak | A61F 13/42 | 340/573.5 |
| 8,893,329 B2 * | 11/2014 | Petrovski | A47C 31/008 | 5/423 |
| 8,978,452 B2 * | 3/2015 | Johnson | A61F 13/42 | 73/74 |
| 9,282,893 B2 | 3/2016 | Longinotti-Buitoni et al. | | |
| 2004/0189331 A1 * | 9/2004 | Girshovich | G01N 27/121 | 324/694 |
| 2005/0261648 A1 * | 11/2005 | Mirle | A61F 13/5376 | 604/381 |
| 2007/0089800 A1 * | 4/2007 | Sharma | D03D 15/0027 | 139/388 |
| 2012/0038375 A1 * | 2/2012 | Kristiansen | G01N 27/02 | 324/694 |
| 2013/0167296 A1 | 7/2013 | Smith | | |
| 2014/0155851 A1 * | 6/2014 | Ales | A61F 13/42 | 604/361 |
| 2014/0340230 A1 * | 11/2014 | Flanagan | A61G 7/057 | 340/604 |
| 2014/0343390 A1 * | 11/2014 | Berzowska | A61B 5/01 | 600/388 |
| 2015/0371522 A1 * | 12/2015 | Mravyan | A61G 7/05776 | 340/573.1 |
| 2016/0000374 A1 | 1/2016 | Dandekar et al. | | |
| 2017/0089853 A1 | 3/2017 | Goenka et al. | | |

OTHER PUBLICATIONS

Pereira et al., Textile moisture sensor matrix for monitoring of disabled and bed-rest patients, EUROCON—International Conference on Computer as a Tool (EURICIN), 2011 IEEE, 4 pp.

BedwettingStore.com, Dry-me Bed-Mat Treatment System, © 2017, http://bedwettingstore.com/dry-me-bed-mat-treatment-system.html, date accessed Jun. 8, 2017, 5 pp.

BedwettingStore.com, Malem ULTIMATE Bed-side Bedwetting Alarm with Pad, © 2017, http://bedwettingstore.com/malem-ultimate-bed-side-alarm-with-pad.html, date accessed Jun. 8, 2017, 7 pp.

Chummie BedWetting Treatment System, Chummie Bedwetting Alarm, © 2017, https://chummiebedwettingalarm.com/, date accessed Jun. 8, 2017, 14 pp.

Easylink UK, Bed Wetting Trainer—Adult Incontinence Alarm, © 2017, http.//www.easylink.co.uk/page53.html, date accessed Jun. 8, 2017, 2 pp.

Lifeline, Enuresis Sensor, © 2017, http://vnclifeline.co.uk/other-vnc-lifeline-products/enuresis-sensor.html, date accessed Jun. 8, 2017, 6 pp.

PottyMD, Wet-Detective Kit with 1 Sensor Pad, © 2017, http://www.pottymd.com/bedwetting-alarms/wet-detective-bed-pad-alarms-sysstems/wetdetec . . . , date accessed Jun. 8, 2017, 4 pp.

Saturn Sales & Services, Ltd . . . Enuresis Sensor, © 1993-2017, https://www.saturn-sales.co.uk/Ensuresis-Sensor.html, date accessed Jun. 8, 2017, 3 pp.

Therapee, The Ultimate Online Bedwetting Treatment, © 2017, Dr. Sagie Bedwetting Clinics, http://www.bedwettingtherapy.com/category/order-therapee, date accessed Jun. 8, 2017, 5 pp.

Vigilant Personal Protection Systems, Vigilant Bed Wetting Urine Alarm Sensor Pad Mat Kit for Nocturnal Enuresis (Extra Large 16.5"×21" Pad-Model PPS-PA21F), © 2017, https://www.vigilantpps.com/products/vigilant-pps-pa21f, date accessed Jun. 8, 2017, 7 pp.

Swaminathan et al., Electrical Characterization of a Textile Sensor for Moisture Detection, Final Degree Thesis, Biomedical Engineering, Thesis No. Jan. 2011, Nov. 2010, 35 pp.

Parkova et al., Fabric Selection for Textile Moisture Sensor Design, Material Science Textile and Clothing Technology, 2012, pp. 38-43.

* cited by examiner

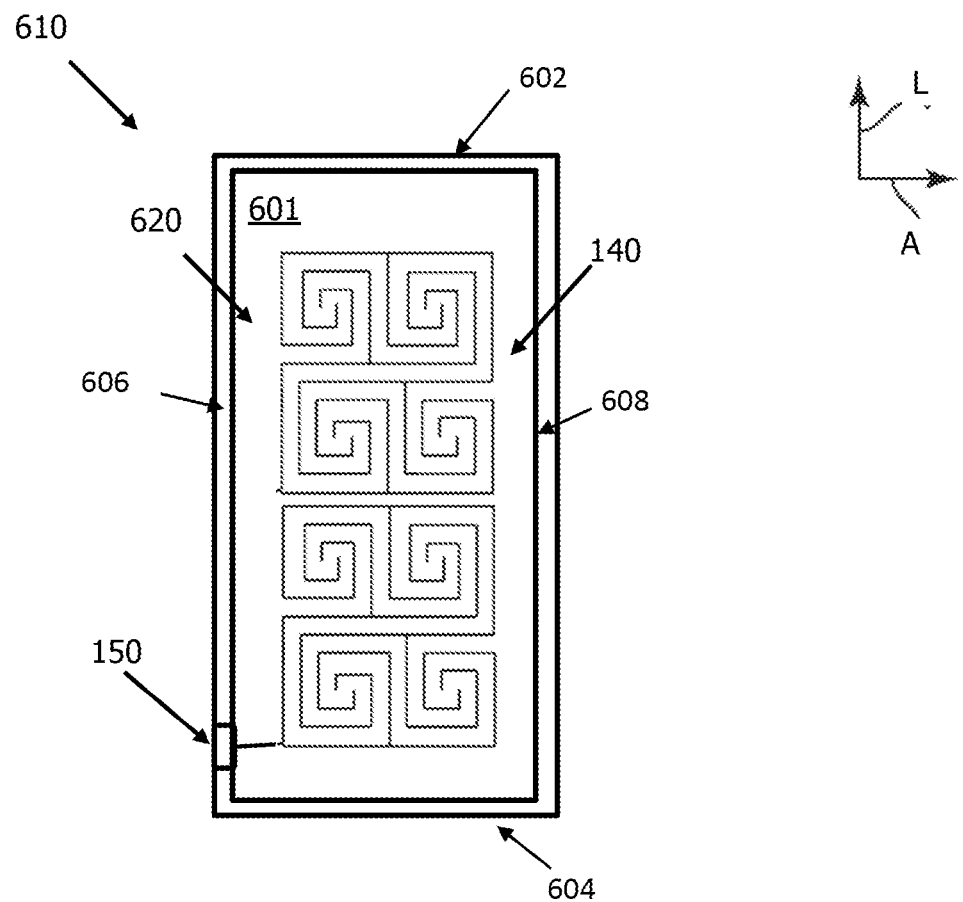
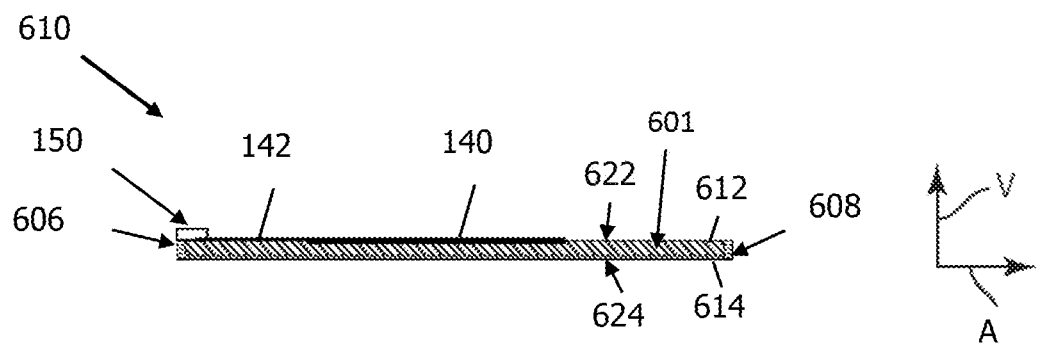
Figure 6A
Figure 6B

TEXTILE ARTICLES AND SYSTEMS FOR LIQUID DETECTION

CROSS-REFERENCE TO RELATED APPLICATIONS

The present application is a continuation of U.S. application Ser. No. 15/275,191, filed Sep. 23, 2016, which claims priority to, and the benefit of, U.S. Provisional Application No. 62/232,443, filed Sep. 25, 2015, the entire disclosures of which are incorporated by reference into the present disclosure.

TECHNICAL FIELD

The disclosure relates generally, but not exclusively, to liquid detection in textile articles using flexible sensors.

BACKGROUND

Textile product, such as garments, bedding, curtains, etc., are ubiquitous products. In a given day, textiles define much of our sensory experience (e.g. sound, sight, touch, smell). But advances in textile technologies have led to new interactions between the user and textiles. For example, wearable technologies include sensors embedded into the fabric structure of a garment that are designed to measure physiological data and transmit that data to a linked computing device. Moisture or liquid detection is another application where sensors are used to detect liquid in a textile material.

SUMMARY

In one embodiment, a system is provided to detect fluid in a textile article. The textile article has a textile material and at least one flexible sensor that obtains sensor data that is indicative of fluid in the textile material that is in contact with the at least one flexible sensor. The at least one flexible sensor includes a conductive element that is integrated into or disposed onto the textile material. The textile article includes an interface element that is electrically connected to the at least one flexible sensor, wherein the interface element is configured to forward the sensor data provided by the at least one flexible sensor to a computing device.

In another embodiment, the system can also include a plurality of textile articles communicatively coupled to a computing device.

The textile articles can be bedding articles, absorbent articles, wound dressings, or other similar articles. Embodiments of the present disclosure also include a method for detecting liquid in at least one textile article (or a plurality of textile articles).

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 6A and 6B are plan and sectional views of a textile article configured as a wound dressing, in accordance with an embodiment of the present disclosure;

DETAILED DESCRIPTION OF EMBODIMENTS

Embodiments of the present disclosure include systems and methods for detecting liquid in textile articles. The textile articles include a textile material and one or more flexible sensors. The flexible sensors include at least one conductive element and are configured to detect the presence of a liquid, such as water or a bodily fluid (e.g. urine, blood or other biological fluids) in the textile article. A textile article as used herein may include any type of article that includes textile materials, such as bedding articles for home or hospital uses, absorbent articles, bandages, wound dressings and the like.

Figure 1A:
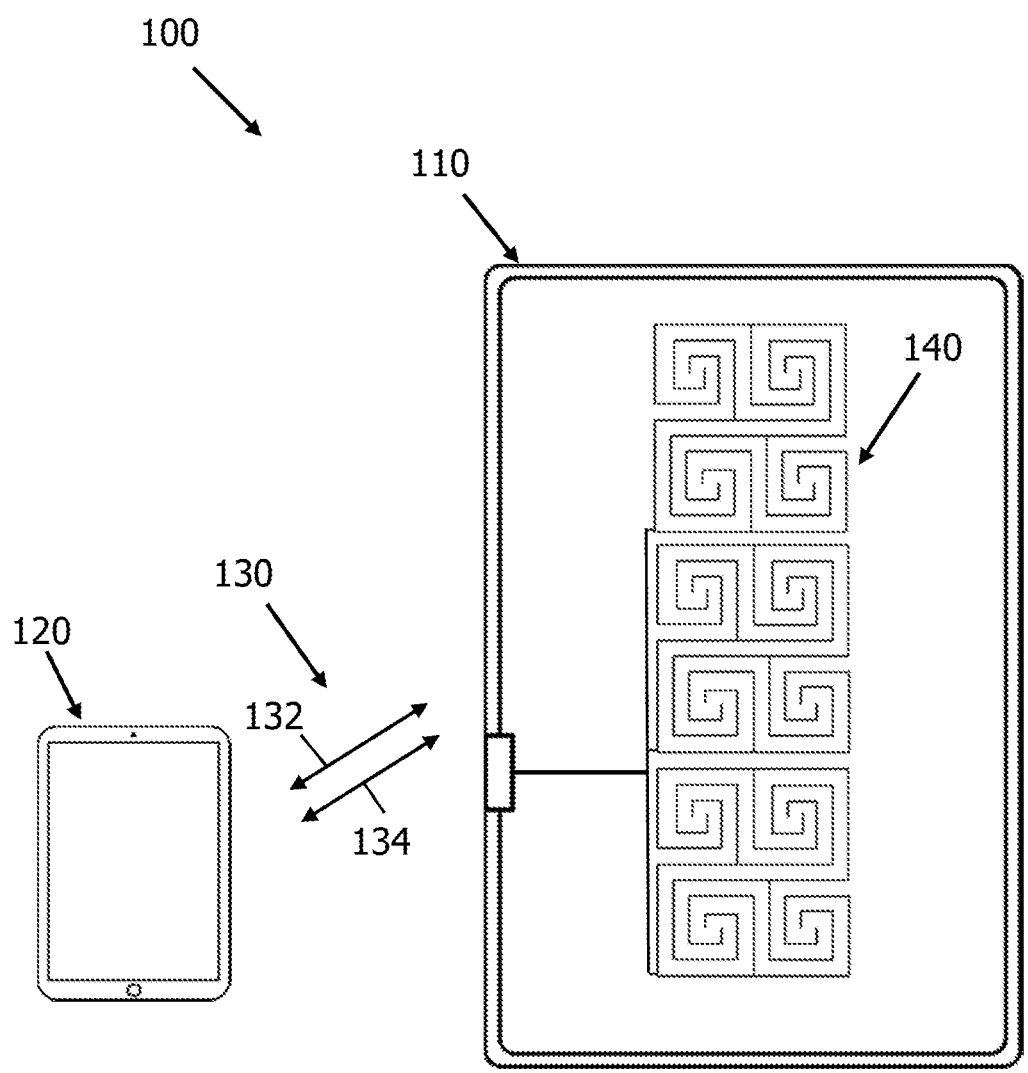
FIG. 1A depicts a system for detecting liquid in a textile article including flexible sensors according an embodiment.

Turning to FIG. 1A, an illustrative system 100 for implementing embodiments of the present disclosure is depicted and referenced generally by designator 100. The components shown in FIG. 1A are a few of the components that embodiments of the present disclosure may interact with during operation. In FIG. 1A, the components are communicatively coupled to each other as appropriate for carrying out their respective functions within system 100. FIG. 1A depicts a high level overview of system 100. Accordingly the components illustrated in FIG. 1A are described with an emphasis on function and in brief for the sake of simplicity. One skilled in the art will recognize that system 100 is but one example of a suitable system for implementing aspects of the invention. As such, system 100 is not intended to suggest any limitation as to the scope of use or functionality of the invention.

As depicted in FIG. 1A, system 100 includes a textile article 110 that is configured to communicate with a computing device 120 through a communications link 130. The textile article 110 includes one or more flexible sensors 140 that are configured to forward sensor data to the computing device 120. The sensor data is indicative of liquid that is in contact with the one or more flexible sensors 140. By using sensors that are flexible and washable, the textile article 110 can have appropriate drape and hand for the intended application while providing the additional functionalities described herein. Typically, sensors used in textile articles are bulky and rigid. In contrast, the textile articles 110 as described herein are drapable and soft even with the flexible sensors 140 integrated into the textile article 110.

Figure 4A:
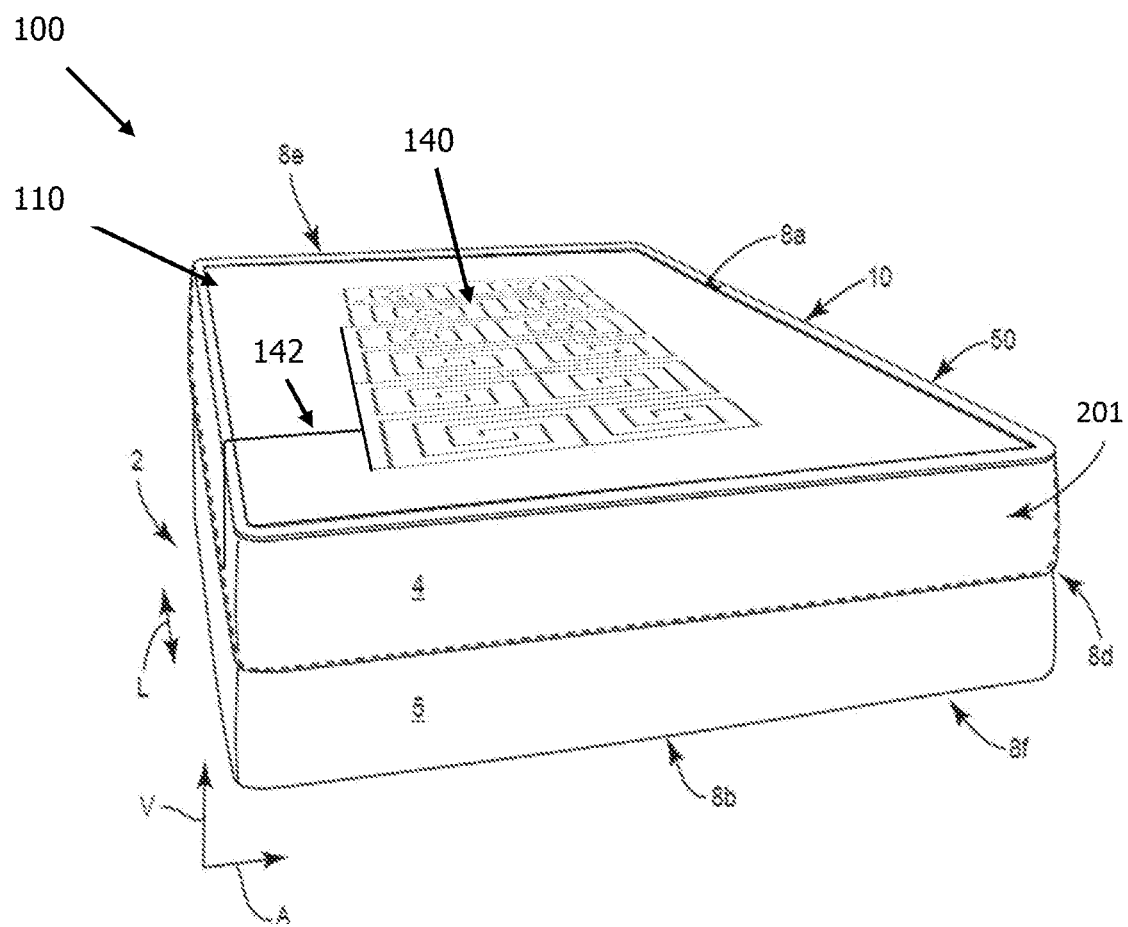
FIGS. 4A, 4B, and 4C are views of a bedding article disposed on a mattress set according to another embodiment.
Figure 4B:
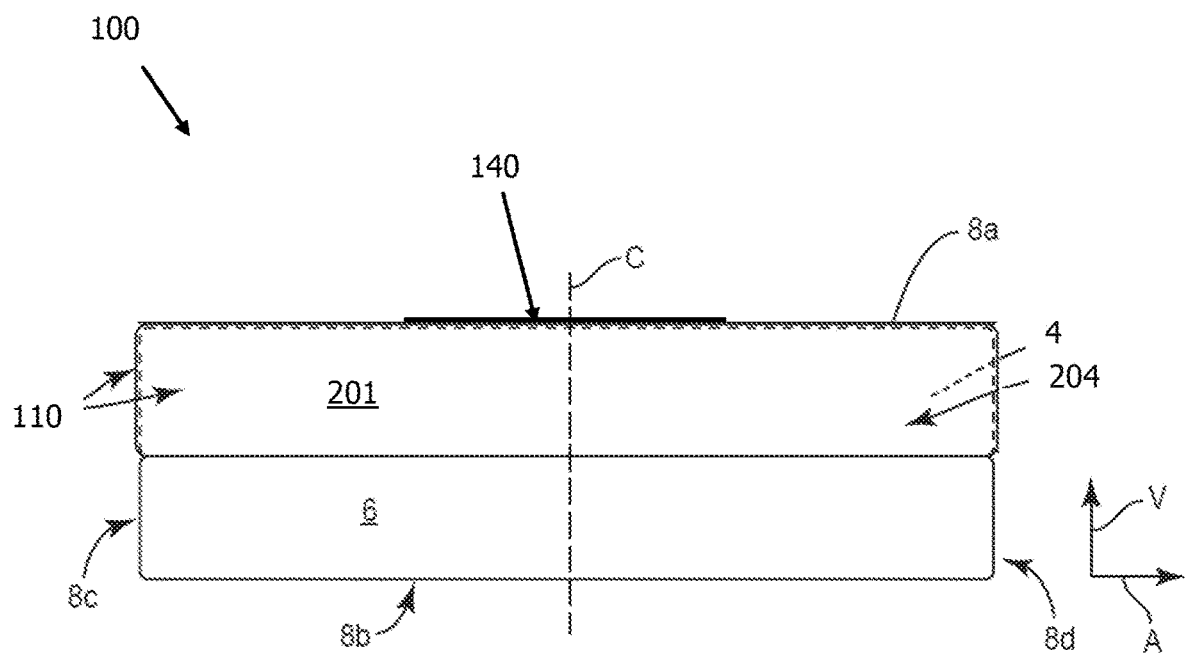

In accordance with the illustrated embodiment in FIGS. 1A-2B, the textile article 110 is a bedding article configured as a bed sheet. A person skilled in the art will recognize that the bedding article may take on any variety of forms. In an alternative embodiment as illustrated in FIGS. 4A and 4B, the textile article 110 may be a mattress pad. Thus, the textile article can by any type of bedding article, including, but not limited to a fitted sheet, blanket, comforter, a quilt, a pillow case, a fitted crib sheet, mattress pad, or any other bedding article that include textile materials that is known in the art.

Referring to FIG. 1A, within the system 100, the computing device 120 is configured to receive the sensor data from the textile article 110 via communication link 130. In response to receiving the sensor data, the computing device 120 is configured to determine if the sensor data indicates that a criterion is met. The phrase "moisture criterion," "liquid criterion" or "criterion" refers to a predefined condition and/or predefined set of conditions referenced by computing device 120 when analyzing sensor data to determine that the textile article 110, or at least one flexible sensor 140, is in contact with liquid or other fluid. In an embodiment, the criterion may be based on an electrical property associated with the flexible sensors 140. The criterion may be based electric conductivity or resistivity. For example, the electrical property may include a resistance, reactance, voltage, current, phase, resonant frequency, or a combination thereof. In another embodiment, a criterion may be based on a measure of variability of an electrical property associated with the one or more flexible sensors. For example, the measure of variability may include range, variance, standard deviation, and the like. In another embodiment, a criterion may be based on a comparison between electrical properties corresponding to two or more flexible sensors.

Referring to FIG. 1A, the communication link 130 represents one or more bidirectional communication paths that communicatively couple the textile article 110 and to the computing device 120. As depicted in FIG. 1, communication link 130 includes downlink direction 132 and an uplink direction 134. Downlink direction 132 represents one or more communication paths from the computing device 120 to textile article 110. Uplink direction 134 represents one or more communication paths from textile article 110 to computing device 120. In an embodiment, communication link 130 is a direct wireless link governed by such communication protocols as: Wi-Fi, Zigbee, Z-Wave, Bluetooth, Bluetooth Low Energy, Near-Field Communications, and the like. In an embodiment, communication link 130 includes at least one wired link governed by such communication protocols as: Ethernet, ATM, Token Ring, FDDI, and the like. In an embodiment, communication link 130 includes at least one telecommunication link governed by such communication protocols as: CDMA, EvDO, GPRS, TDMA, GSM, WiMax technology, LTE, LTE Advanced, and the like. The communication link 130 can include a wired link as well.

The communication link 130 includes a network of any type that is suitable for providing communications the textile article 110 and computing device 120. In this embodiment illustrated in FIG. 1A, the communication link 130 may comprise a combination of discrete networks which may use different technologies. For example, the communications network includes a cellular network, a Wi-Fi/broadband network, a local area network (LAN), a wide area network (WAN), a telephony network, a fiber-optic network, or combinations thereof. In an example embodiment, communication link 130 includes the Internet and any networks adapted to communicate with the Internet. Communication link 130 may be also configured as a means for transmitting data between textile article 110 and computing device 120.

Figure 1B:
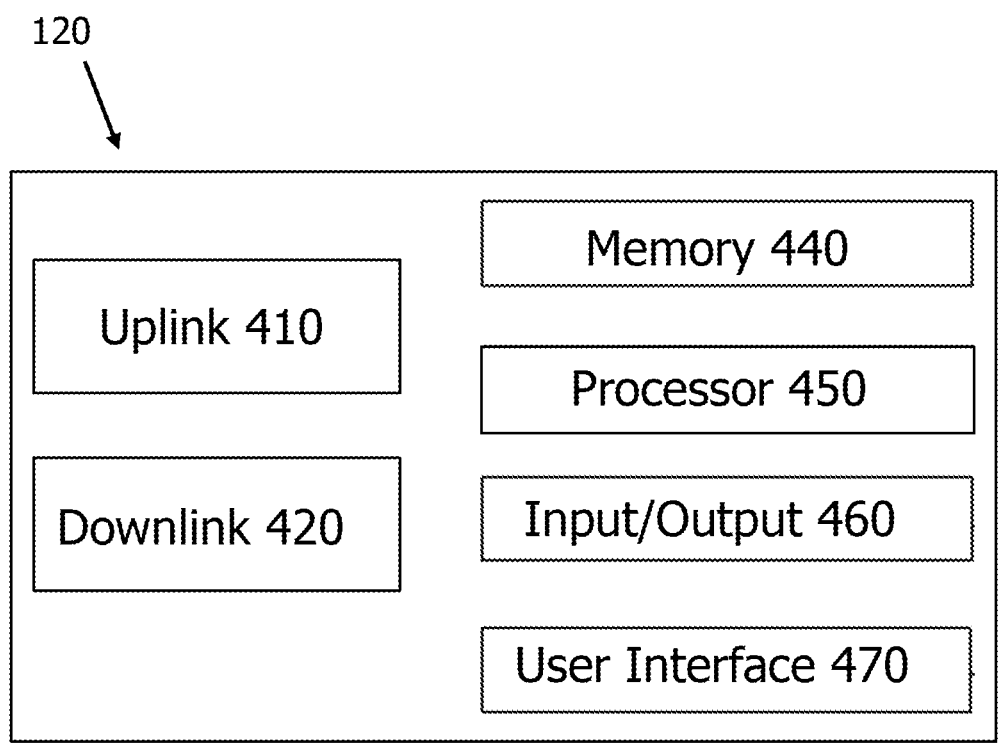
FIG. 1B is a block schematic diagram of a computing device shown in FIG. 1A.

Referring to FIG. 1B, the system 100 may include a computing device 120. As illustrated, the computing device 120 is depicted as a smart phone. However, the computing device 120 can be any computer device and can take on a variety of forms. For example, computing device 120 may take on the form of a desktop computer, a laptop, a tablet, or any other computing device known in the art. The computing device 120 can be referred to as a monitoring device.

Continuing with FIG. 1B, the computing device 120 is configured to receive, process, and store information used to implement one or more software applications that can determine presence of liquid in the textile articles as described herein. As depicted, the computing device 120 includes an uplink port 410, a downlink port 420, a memory 440, one or more computer processors 450, an input/output portion 460, and a user interface 470. It should be appreciated by those skilled in the art that the functionality of computing device 120 implemented through processor executable instructions may readily be converted into a hardware implementation by well-known design rules in the electrical engineering and software engineering arts. For example, the functionality of computing device 120 described herein can be converted into a hardware implementation using application-specific integrated circuits, microcontrollers, field programmable gate arrays, digital signal processors, and the like. Those skilled in the art will likewise recognize that the functionality of computing device 120 may readily be implemented through a hybrid approach composed of combination of hardware and software techniques.

In a networked environment, uplink port 410 is configured to serve as an endpoint for one or more communication paths in an uplink direction of a communication link (e.g. uplink direction 134 of FIG. 1A) from a textile article to computing device 120. In an embodiment, sensor data indicative of liquid is received by computing device 120 from the textile article via uplink port 410. In the networked environment, downlink port 420 is configured to serve as an endpoint for one or more communication paths in a downlink direction 132 of the communication link 130 from the computing device 120 and the textile article. In one example, messages are sent by computing device 120 to the textile article via downlink port 420. Such messages, for example, may include instructions to feed an excitation signal to one or more flexible sensors integrated in the bedding article. As another example, the messages can include feedback indications responsive to received sensor data and communication protocol related messages, such as: connection requests/responses, acknowledgements, sequencing information, and the like.

Continuing with FIG. 1B, in various embodiments, the input/output portion 460 is coupled to uplink port 410 and downlink port 420. The input/output portion 460 may include an antenna, electronic connector for wired connection, or a combination thereof, a receiver and transmitter, transceiver, and/or transmitter-receiver. The input/output portion 460 is capable of receiving and/or providing information pertaining to communication with a network such as, for example, the Internet. As should be appreciated, transmit and receive functionality may also be provided by one or more devices external to the computing device 120. The input/output portion 460 may also include, for example, a network interface controller, modem, various modulators/demodulators and encoders/decoders, wireless and wired interface cards, and the like.

Continuing with FIG. 1B, in accordance with the illustrated embodiment, the input/output portion 460 includes a transceiver coupled to the uplink port 410 and the downlink port 420. The transceiver is configured to enable communication between computing device 120 and the textile article. In one respect, transceiver enables communication by establishing the communication link 130 between computing device 120 and the textile article. For example, transceiver may send a connection request to an endpoint for the one or more communication paths associated with the bedding article via downlink port 420. As another example, transceiver may respond to a connection request received from the textile article in the uplink direction via uplink port 410. Transceiver can also enable communication by decoding electrical signals according to a communication protocol associated with the communication link or encoding data from processor 450 according to the communication protocol.

Continuing with FIG. 1B, memory 440 is coupled to and configured to provide nonvolatile and volatile storage for the various components (e.g. processor 450 and transceiver) of computing device 120. For example, memory 440 may provide storage of processor executable instructions, data structures, program modules, software applications, sensor data, and other data for use by the various components of computing device 120. In embodiments, memory 440 may be implemented with one or more of the following: random access memory (RAM); a storage device (e.g. electromechanical hard drive, solid state hard drive, etc.); firmware; removable storage devices (e.g. optical storage discs, flash memory, external storage devices, etc.); and the like.

Referring still to FIG. 1B, one or more processors 450 are coupled to transceiver and memory 440. The processor 450 (or a plurality of processors) is configured to execute a software application that determines if moisture is present in the textile article based on received sensor data. As noted above, sensor data indicative of liquid in the textile article is received by a transceiver. In an embodiment, processor 450 is configured to detect fluid in the bedding article by performing the method described below with respect to FIG. 8.

Referring to FIG. 1B, the user interface 470 can include an input device and/or display (input device and display not shown) that allows a user to communicate with the computing device 120. The user interface 470 can include inputs that provide the ability to control the computing device 120, via, for example, buttons, soft keys, a mouse, voice actuated controls, a touch screen, movement of the computing device 120, visual cues (e.g., moving a hand in front of a camera on the computing device 20), or the like. The user interface 470 can provide outputs, including visual displays. Other outputs can include audio information (e.g., via speaker), mechanically (e.g., via a vibrating mechanism), or a combination thereof. In various configurations, the user interface 470 can include a display, a touch screen, a keyboard, a mouse, an accelerometer, a motion detector, a speaker, a microphone, a camera, or any combination thereof. The user interface 470 can further include any suitable device for inputting biometric information, such as, for example, fingerprint information, retinal information, voice information, and/or facial characteristic information, for instance, so as to require specific biometric information for access to the computing device 120. It should be appreciated that the computer devices can operate via any suitable operating system, such as Android, BSD, iOS, Linux, OS X, QNX, Microsoft Windows, Windows Phone, and IBM z/OS. Furthermore, the software application can operate with any of the aforementioned operation systems.

The system 100 may include at least one software application running on the computing device 120. The software application is configured for execution by a computer processor that is in electronic communication with the interface element 150 of the textile article 110. The software application is further configured to, in response to receiving sensor data from the textile article, a) determine if the sensor data indicates that a criterion is met, and b) based on the determination that the criterion is met, determine if a respective one of the at least one flexible sensors is in contact with liquid.

Figure 2A:
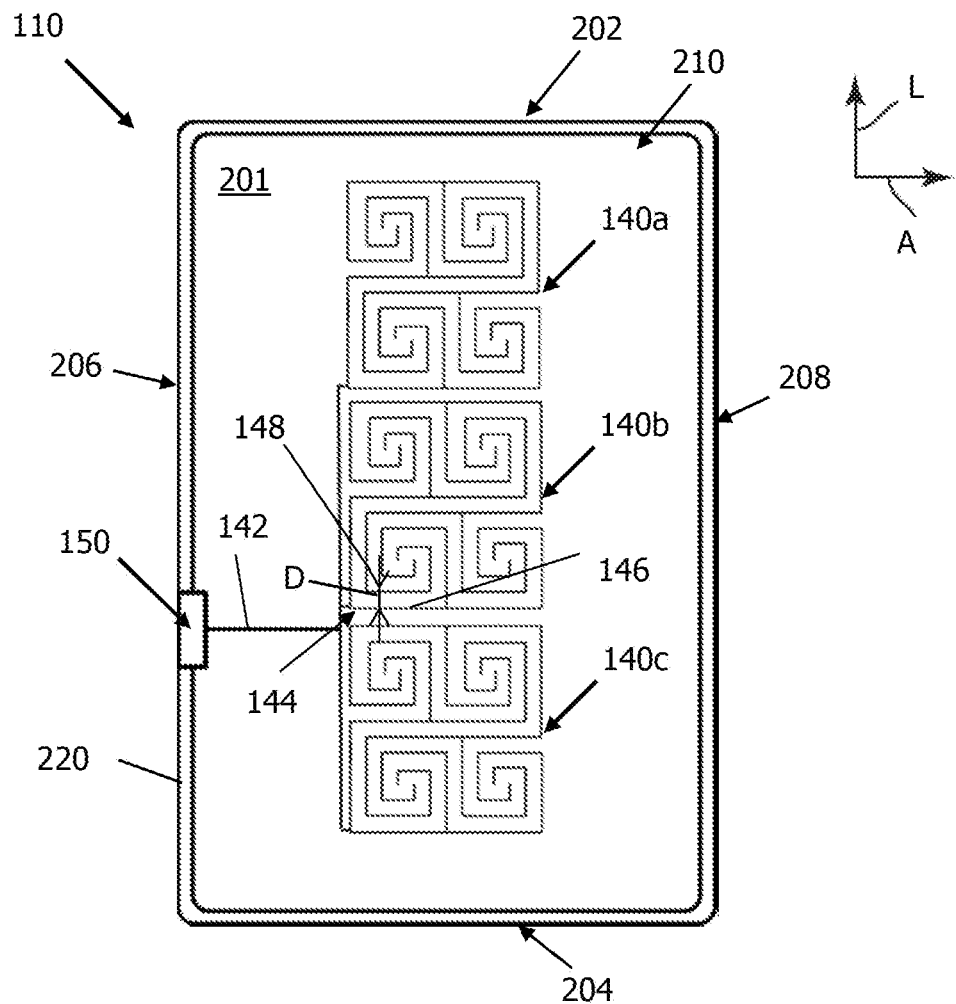
FIG. 2A is a plan view of the textile article shown in FIG. 1A.

Turning to FIG. 2A, in accordance with an embodiment of the present disclosure, the textile article 110 includes a textile material 201, one or flexible sensors 140 integrated into or on the textile material 201, and an interface element 150. The interface element 150 can be a data conduit between the flexible sensors 140 and the computing device 120. Each component will be discussed next.

Figure 2B:
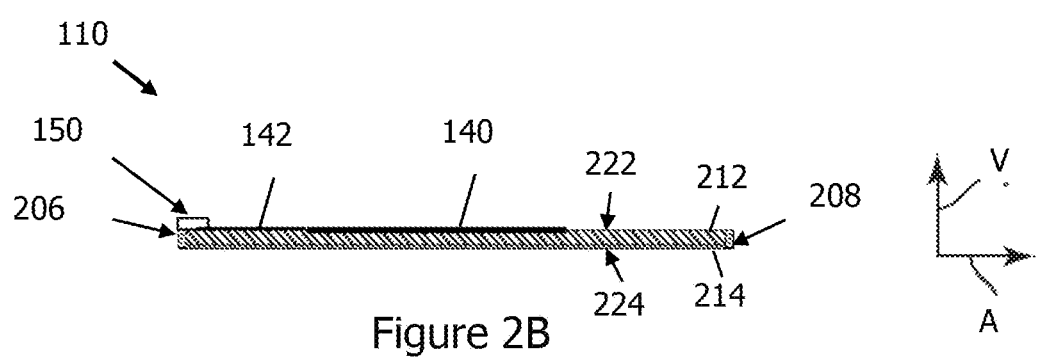
FIG. 2B is a sectional view of the bedding article shown in FIG. 2A.
Figure 3A:
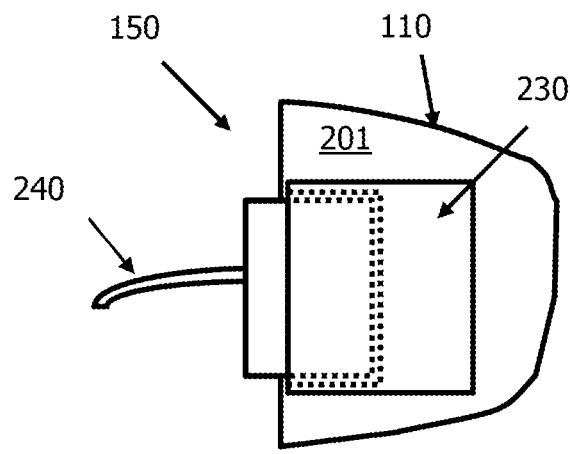
FIGS. 3A and 3B are top views of a connector of the textile article shown in FIG. 1A.
Figure 3B:
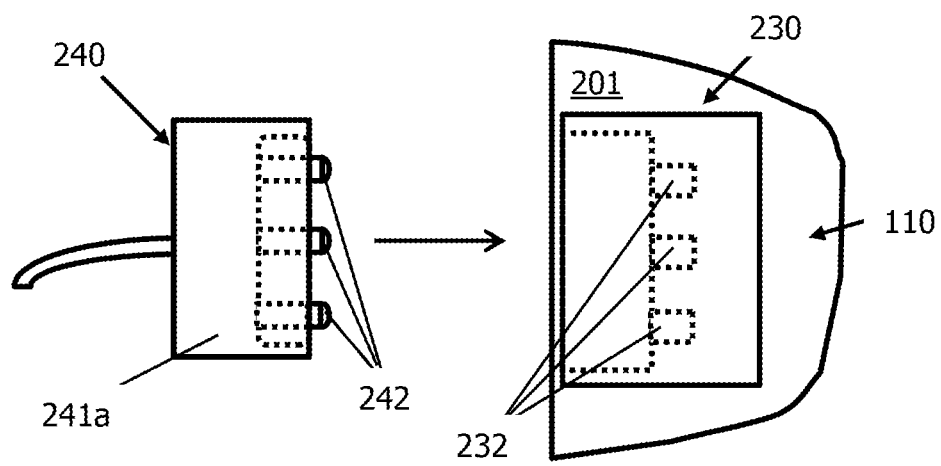
Figure 3C:
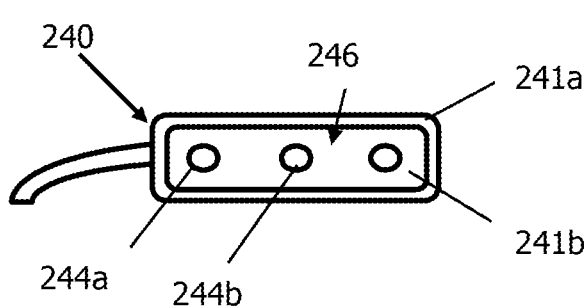
FIG. 3C is an end view of a first portion of the connector shown in FIGS. 3A and 3B.
Figure 3D:
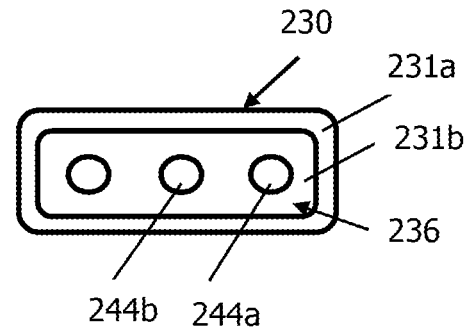
FIG. 3D is an end view of a second portion of the connector shown in FIGS. 3A and 3B.

Continuing with FIGS. 2A and 2B, the textile article 110 includes the textile material 201 in the form of a panel 210. The panel 210 has a first end 202, a second end 204 spaced from the first end 202 along a longitudinal direction L, and opposed side ends 206 and 208, respectively, spaced apart with respect to each other along a lateral direction A that is perpendicular to the longitudinal direction L. The panel 210 also includes a face 212 and a back 214 opposed to a face 212 along vertical direction V. The panel 210 is framed by hem 220 along an external perimeter of the panel 210. When hem 220 is present, the interface element 150 may be attached to textile article 110 along or proximate to the hem 220.

Figure 4C:
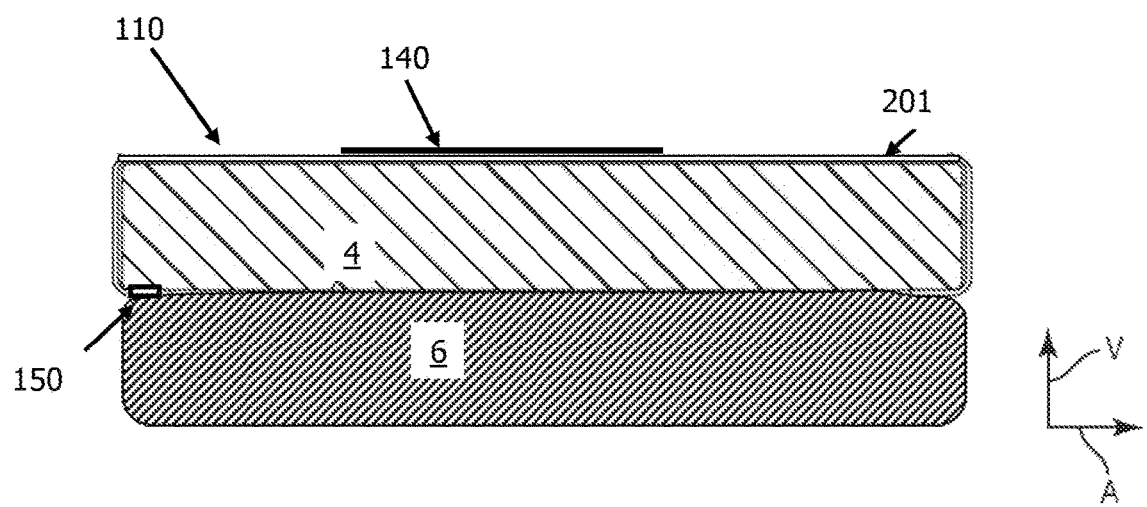

The textile material 201 further includes at least one textile layer 222 that defines the face 212 and at least one optional barrier component 224 disposed adjacent to the at least one textile layer 222. The barrier component 224 defines the back 214 of the textile material 201. When the textile article 110, for example a bedding article, is placed on the mattress as shown in FIGS. 4A-4C, the barrier component 224 is configured to block or inhibit moisture from traveling through the back 214 of the textile material 201 into the mattress.

The textile layer 222 can be a woven, knit, or nonwoven fabric, or any combination thereof. In one example, the textile layer 222 is a woven fabric having a plurality of warp yarns and a plurality of weft yarns interwoven with the plurality of warp yarns to define the woven fabric. Any type woven construction could be used, such as a plain weave, satin/sateen, twill, basket weave, or any other suitable woven construction. In one example, the plurality of warp yarns are arranged to define a warp end density between about 50 warp ends per inch and about 300 warp ends per inch. The weft yarns are arranged to define a weft density between about 50 picks per inch and about 300 picks per inch. Woven fabrics can include synthetic warp and weft yarns, natural or blended warp and weft yarns, synthetic warp yarns with natural and/or blended weft yarns, natural warp yarns with synthetic weft yarns. The warp yarn can have a range of yarn counts. For instance, in one example, the warp yarn can have a count in a range between about 50 denier (106 Ne) to about 250 denier (21 denier). The weft yarns can have a range of yarn counts. For instance, in one example, the weft yarn has a count in a range between about 50 denier (106 Ne) to about 250 denier (21 denier).

In another example, the textile layer is a knit fabric. Knit fabrics may be a weft knit, such as single jersey knit fabric, a double knit, rib knit, or any other type of weft knitted fabric. The knit fabric may alternatively be a warp knit, such as a tricot or Rachel warp knitted fabric. Yarns used in the knit fabric can have a range of yarn counts. For instance, in one example, the knit yarn can have a count in a range between about 50 denier (106 Ne) to about 250 denier (21 denier).

The textile layer 222 when woven or knit can be formed from any number of yarn types, such a spun yarns or continuous filament yarns. Spun yarns may include natural fibers, synthetic fibers, or blends of natural and synthetic fibers. Natural fibers include cotton, wool, bamboo, flax, hemp, or others. Synthetic fibers may include polyethylene terephthalate (PET), polyolefin, polyamide 6, polyamide 6,6, polylactic acid (PLA) fibers, viscose rayon, acrylic, or other fiber types, such a flame resistant fibers as needed. Suitable thermoplastic synthetic staple fibers may be mono-component or bi-component type fibers. A variety of yarn spinning types can be used, such as ring spun, open end, air-jet, compact spinning, and the like. Continuous filaments yarns may include either or both mono-component or bicomponent filaments types. Continuous filament yarns can be polyethylene terephthalate, polyolefin, and/or polyamide 6, polyamide 6,6, polylactic acid filaments.

The textile layer 222 may also be a nonwoven fabric. Suitable nonwoven fabrics include melt-spun nonwovens, such as spunbond and meltblown materials or other structures. A meltspun nonwoven can include a single spunbond layer, multiple spunbond layers, a single meltblown layer, multiple meltblown layers, or multiple layers of spunbond and meltblown materials. Meltspun nonwovens can from with polyethylene terephthalate, polyolefin, and/or polyamide 6, polyamide 6,6, or polylactic acid polymers. Alternatively, the nonwoven fabrics can be carded or airlaid materials that are bonded thermally, chemically, and/or mechanically, e.g. via needles or stitch bonding. Suitable fibers for carded or airlaid materials include PET and viscose fibers, and the like.

The textile layer 222 could also be laminate of a woven and nonwoven fabric, a knit and nonwoven fabric, or even a woven and knit fabric. The textile layer 222 may also include a number of functional finishes, coatings, or other treatments that enhance functionality. For instance, the textile layer 222 can include anti-bacterial agents, coatings, flame retardant coatings, and the like.

The barrier component 224 can be a finish, coating, fabric, or film or membrane coupled to one side of the textile layer 222. The barrier component is configured to help inhibit penetration of moisture or liquid through the article 110, as discussed above. In one example the barrier component is a fluorocarbon finish applied to one side of the textile layer 222. In another example, the barrier component is a fabric with a fluorocarbon carbon finish applied to one side of the fabric.

Referring to FIGS. 1-2B, the flexible sensors 140 can provide sensor data indicative of liquid in contact with the sensors 140. The flexible sensors 140 may have flexural properties, rigidity, and softness that approximate the flexural properties, rigidity, and softness of the textile material 201 to which they are integrated or disposed upon. In one example, the flexible sensors 140 have flexural properties, rigidity, and softness that is substantially similar to the flexural properties, rigidity, and softness of the textile material 201 to which they are integrated or disposed upon. The flexible sensors 140 may also be considered textile sensors. The flexible sensor 140 may include at least one conductive element 144 arranged in a pattern. As illustrated, the flexible sensor 140 includes interface leads (not shown) and/or a wire connector 142. The wire connector 142 is electrically coupled to the two interface leads on the flexible sensor 140 and interconnects with the interface element 150.

Referring FIGS. 1-2B, the conductive element 144 is configured to propagate electrical signals (e.g. an excitation signal) to the interface element 150. The conductive element 144 includes at least one first linear portion 146 and at least one second linear portion 148 that is spaced apart from the at least one first linear portion a distance D. In some examples, the distance D is between 0.5 cm to about 5.0 cm. The distance D can be any particular range of distances between 0.5 cm to 5.0 cm. For instance, the distance D can be between: 0.5 to 1.0 cm; 0.5 to 1.5 cm; 0.5 to 2.0 cm; 0.5 to 2.5 cm; 0.5 to 3.0 cm; 0.5 to 3.5 cm; 0.5 to 4.0 cm; 0.5 to 4.5 cm; 1.0 to 5.0 cm; 1.5 to 5.0 cm; 2.0 to 5.0 cm; 2.5 to 5.0 cm; 3.0 to 5.0 cm; 3.5 to 5.0 cm; 4.0 cm to 5.0 cm; and/or 4.5 to 5.0 cm. In some alternative embodiments, the distance D can be less than about 0.5 cm. For instance, the distance D can be between 0.2 cm and about 0.5 cm.

When a conductive liquid is exposed to the textile material 201 in the region between adjacent sections of the first and second linear portions 146 and 148, respectively, the liquid completes a circuit between the first and second linear portions 146 and 148 of the conductive element 144. The completion of the circuit results in an output signal propagated to the interface element 150 via the wired connector 142, as further described below.

The illustrated embodiment is a conductive-type of flexible sensor whereby presence of liquid completes a circuit. In alternative embodiment, the flexible sensors can be configured as resistivity type sensors. Resistivity type sensors may have two wire connectors coupled to the two interface leads. The presence of liquid between two portions of the flexible sensor adjusts the resistivity of the sensors as detected by the interface element. The signal received the interface element may be resistivity, or resistivity fluctuation.

The conductive element and first and second linear portions 146 and 148 can have any particular pattern or shape. As illustrated in FIGS. 1-2B, the first and second linear portions 146 and 148 can be arranged in a spiral pattern. In an alternative embodiment, the conductive element 144 can be arranged to have a "comb type" configuration. For example, in a comb-like configuration (not shown), the conductive element 144 can have a linear base portion that is elongate along a select direction, and one or more branch portions that extend from the base portion in a direction that is angularly offset with respect to the select direction. "Angularly offset" as used herein means an angular direction (or axis) that is acute, right, and/or obtuse with respect to a reference direction (or axis). The conductive element can have any design or pattern as needed.

The conductive element 144 can be any generally flexible material that is adapted to be electrically conductive. For instance, the conductive element can be a fiber, yarn, textile material, laminate, or other material that is electrically conductive. In one example, the conductive element 144 is a conductive yarn. The conductive yarn may be a twisted assembly of stainless steel fibers. In another example, the conductive yarn is formed as a continuous filament yarn formed from a polymer with conductive particles embedded into the polymer. In such an example, the conductive particles are embedded so that filamentary stricture is electrically conductive. In such an example, adjacent conductive particles may be in contact with each other along a length of the filament and across a width of the filament, such that an electrical signal can travel along the filament. The conductive yarn may be a polymer filament with a conductive coating around an outer periphery of the filament. In another example, the conductive yarn can be a staple fiber yarn with a conductive outer sheath. The conductive yarn can also be a staple fiber yarn having an outer sheath of fibers (absorbent or synthetic) and an electrically conductive core. The conductive yarn can also be a staple fiber yarn having conductive polymer staple fibers that include conductive particles within the fiber.

The conductive yarn may be embroidered onto the textile layer 222 in a defined pattern as illustrated in FIGS. 1-2B. For instance, a conductive yarn can be embroidered into the textile material 201 to so as to have at least one first linear portion 146 and at least one second linear portion 148 that is spaced apart from the at least one first linear portion a distance D as described above.

In another example, the conductive yarns may be used as part of the fabric structure to form the flexible sensors. The conductive yarn can be inlayed through certain regions in a woven fabric design to create the desired sensor pattern. For instance, a complex triple layer woven fabric can be designed so that a conductive region is created using conductive yarns arranged in a defined sensor pattern. In such an exemplary woven fabric, the conductive region defines a conductive pattern that includes at least one first linear portion 146 and at least one second linear portion 148 that is spaced apart from the at least one first linear portion a distance D as described above. Woven jacquard sensors can be created to form a conductive region made of conductive yarns. In such woven jacquard, the conductive region defines a conductive pattern that includes at least one first linear portion 146 and at least one second linear portion 148 that is spaced apart from the at least one first linear portion a distance D as described above. In yet another example, for knitted fabrics, a conductive yarn can be selectively inlayed into certain needles during knitting to create consecutive and adjacent stitches that define a conductive region. In such an example of a knit fabric, the conductive regions define a conductive pattern that includes at least one first linear portion 146 and at least one second linear portion 148 that is spaced apart from the at least one first linear portion a distance D as described above. In another example, the conductive yarns can be used in a warp knit fabric to form an arrangement of warp knit stitches that define a conductive region that defines a sensor pattern. In such an example of a warp knit fabric, the conductive region defines a conductive pattern that includes at least one first linear portion 146 and at least one second linear portion 148 that is spaced apart from the at least one first linear portion a distance D as described above.

In another example, the conductive element is a conductive ink that is printed onto the textile material. In such an example, the conductive inks can be printed onto the textile material so as have at least one first linear portion 146 and at least one second linear portion 148 that is spaced apart from the at least one first linear portion a distance D as described above.

In another example, the conductive element can be a conductive laminate that includes conductive materials. The conductive laminate may include a flexible textile material and a conductive layer, such as a copper or another other metal deposited on to the textile material. The conductive laminate can be cut or formed into any desired pattern and adhered to the textile material. The conductive laminate can be adhered with an adhesive, stitched, thermally adhered, or ultrasonically adhered to the textile layer. In one example, the conductive laminate can have a conductive region that includes at least one first linear portion 146 and at least one second linear portion 148 that is spaced apart from the at least one first linear portion a distance D as described above.

In such an example, the conductive laminate may be perforated so that liquid can access the conductive materials and complete the circuit to propagate a signal to the interface element 150 as described above.

Continuing with FIGS. 1-3, the interface element 150 includes a connector 230, a PCB for electric components, a transceiver, and a power source, and/or connection for a power source. In accordance with the illustrated embodiment, the interface element 150 includes a connector 240 that is configured for both data and power transmission such that the connector 240 serves as part of a data link and connection to a power source.

Turning to FIGS. 3A-3D, the system 100 includes a first connector 230 and a second connector 240. The first connector 230 is configured as part of the interface element 150 as described above. The second connector 240 is a wired connector that can be coupled to a power supply and/or to the computing device 120 via a communications link.

The first connector 230 includes a plurality of contacts 232. The first connector may include a body 231*a* that includes a cutout region 231*b*. The contacts 232 are located inside the cutout region 231*b*. The contacts 232 extend into the body 231*a* and are connected to one or more traces on the PCB of the interface element 150. The plurality of contacts 232 includes at least a first contact 234*a* that is configured for power transmission and at least one second contact 234*b* that configured for data transmission. The first contact 234*a* is coupled to the PCB (not shown) and the second contact 234*b* is coupled to at least the transceiver (not shown). As shown, the first connector 230 is in the form of a male connector and the second connector 240 is in the form of a female connector.

The second connector 240 may be a power and data connector that is configured to be coupled to the first connector of the interface element 150. The second connector 240 includes a plurality of contacts 242 that are configured to engage the plurality of contacts 232 of the interface element 150. The second connector also includes a body 241*a* with a cutout region 241*b* that houses the contacts 242. The body 241*a* of the second connector is configured to mate with the cutout region 231*b* of the first connector. In the embodiment illustrated, the second connector can be coupled to receive electrical power from external power sources, such as external batteries, electrical outlets, and the like.

In certain embodiments, the connector 230 is configured to be magnetically coupled to second connector 240. Accordingly, the first connector 230 includes a magnetic portion 236 (e.g. a magnetic surface) configured to couple to a magnetic portion 246 (e.g. magnetic surface) of the second connector 240. In an alternative embodiment, however, the first connector 230 includes a mechanical coupler, such as a snap-fit, that is configured to couple to a mechanical coupler (not shown) of the second connector 240.

In alternative embodiments, the interface element 150 comprises an internal power source (not shown) configured to provide electrical power to the various components of textile article 110. For example, the internal power source may be implemented as: a battery; a storage capacitor; a small-scale energy source (e.g. piezoelectric, magnetic induction, or thermoelectric generators); and the like. The internal power source may be attached to the textile article 110 along hem 220.

In one example, the textile article 110 is a bedding sheet and the textile material 201 is a woven fabric is formed with cotton warp and weft yarns. The weight can be about between 100 and 200 grams per square meter and has a construction between 20 to 60 EPI and about between 20. In such an example, the barrier component is a fluorocarbon carbon finish applied to the woven fabric. A conductive yarn composed of stainless steel fiber is embroidered onto the woven fabric in pattern as illustrated in FIGS. 1 and 2B. The interface element 150 is coupled to the hem 220 and wired connector 142 couples the flexible sensor 140 to the interface element 150.

The textile articles as described herein could be used to monitor nocturnal enuresis or bedwetting. Bedwetting is common among young children and is one area were textile articles as described here may prove beneficial to reduce or eliminate occurrences of nocturnal enuresis.

FIGS. 4A and 4B illustrates the textile article 110 applied to a mattress set 2 that includes a mattress 4 and box springs 6. The mattress set 2 includes a top 8a, a bottom 8b spaced from the top 8a along a vertical direction V, opposed sides 8c and 8d spaced apart with respect to each other along a lateral direction A, a first end 8e and second end 8f opposed to the first end 8e along a longitudinal direction L that is perpendicular to the vertical and lateral directions V and A. As shown in FIGS. 4A-4C, the textile article 110 is configured to wrap around the sides 8c, 8d, and first and second ends 8e and 8f of the mattress. As illustrated, the interface element 150 is positioned along a hem 220 such that the interface element 150 is disposed between the mattress top 4 and box springs 6 such that the interface element 150 is hidden from view.

In operation, the computing device 120 is adapted to determine if moisture is present in the textile article 110 based on sensor data received from the flexible sensors 140. When moisture contacts first and second linear portions 146 and 148 of the flexible sensor 140, the flexible sensor 140 generates a data signal indicative of liquid. The interface element 150 forwards the sensor data indicative of liquid to the computing device 120 via a communication link communication link 130. In one respect, interface element 150 is configured to serve as an endpoint for one or more communication paths of the communication link between textile article 110 and the computing device. In an embodiment, interface element 150 serves as the endpoint by implementing one or more of a network interface controller, a modem, a modulator, a demodulator, an encoder, a decoder, a wireless interface card, a wired interface card, and an antenna.

In embodiments utilizing excitation signals, interface element 150 is further configured to generate and feed excitation signals to one or more of the flexible sensors 140. In one example, an excitation signal is continuously generated and fed to at least one of the textile sensors 140 by interface element 150. In another example, an excitation signal is periodically generated and fed to at least one of the textile sensors 140. Regardless, the excitation signal is generated and fed to at least one of the flexible sensors 140 in response to receiving an instruction to do so. For example, such instruction may be received from the computing device 120. In another example, such instruction may be received from a component within interface element 150 according to a predefined metric. The predefined metric may be based on interface element 150 detecting movement, a temperature change, activation of an input associated with textile article 110 (e.g. a button), and the like.

Figure 5A:
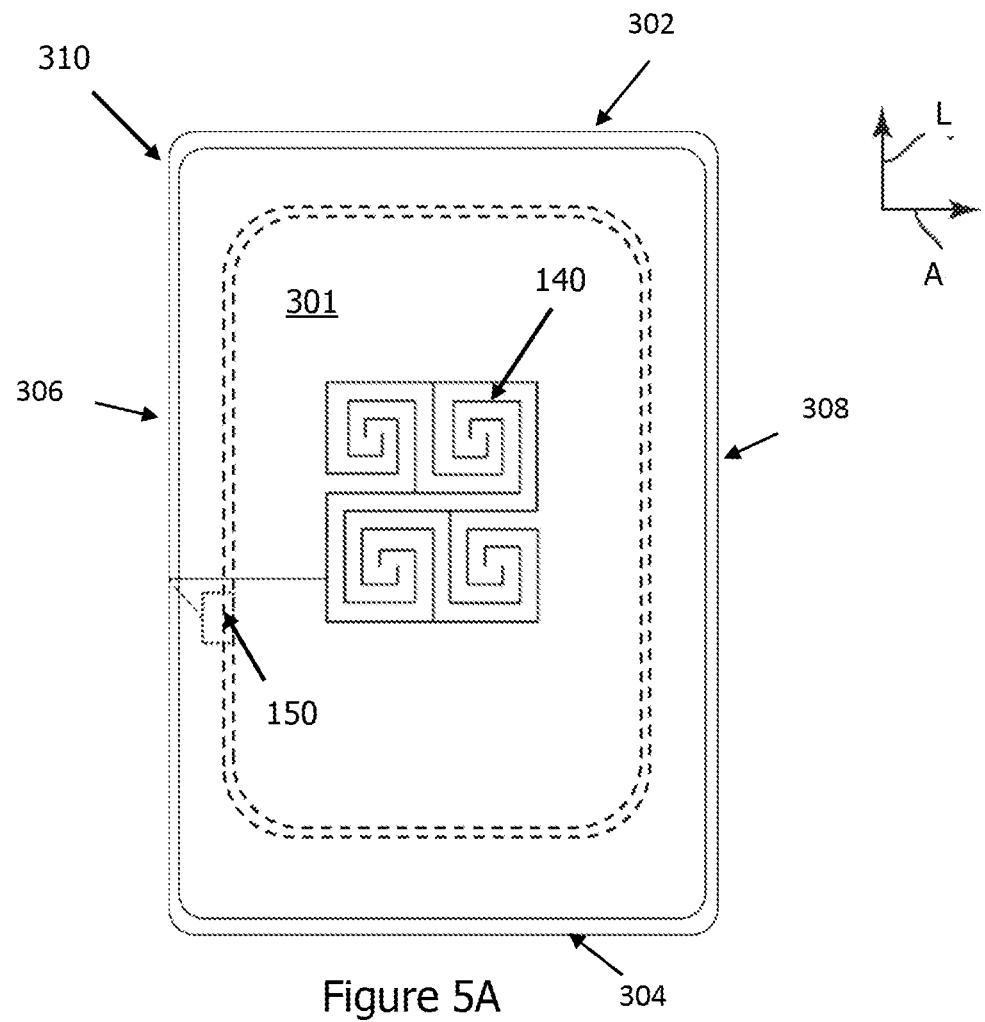
FIGS. 5A and 5B are plan and sectional views, respectively, of a mattress cover or pad including a flexible sensor, in accordance with another embodiment.
Figure 5B:
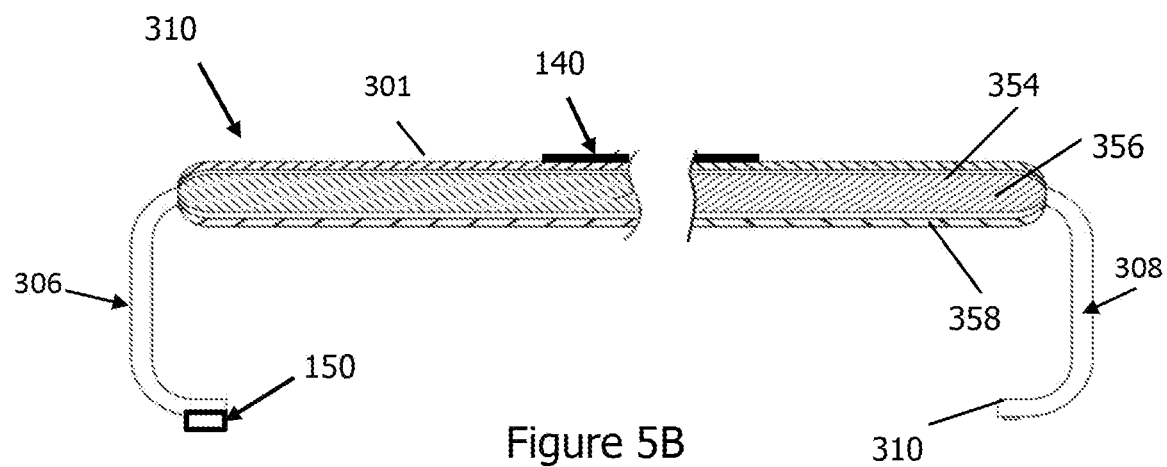

According to another embodiment shown FIGS. 5A and 5B, a textile article 310 is configured as a mattress cover or pad that can overly the top panel of the mattress. The textile article 310 includes one or more flexible sensors 140 and an interface element 150. The flexible sensors 140 and interface element 150 shown in FIGS. 5A and 5B are similar to the flexible sensors 140 and interface element 150 described above.

Continuing with FIGS. 5A and 5B, the textile article 310 includes a panel 301 an upper layer 354, a lower layer 358 opposed to the upper layer 354, and a cushioning member 356 disposed between the upper and lower layers 354 and 358. Either or both the layers 354 and 358 may include a barrier component that is similar to component 222 described above. Accordingly, the barrier component can be a finish, coating, fabric, or film or membrane. The barrier component is configured to inhibit penetration of liquid through the article 310, as discussed above. In one example the barrier component is a fluorocarbon finish applied to one side of the textile material. In another example, the barrier component is a fabric with a fluorocarbon carbon finish applied to one side of the layer 354 or 358.

Continuing with FIGS. 5A and 5B, the panel 301 further includes a first end 302, a second end 304 spaced from the first end 302 along the longitudinal direction L to define a length 53, and opposed sides 306 and 308 spaced apart with respect to each other along the lateral direction A. As illustrated, the panel 301 is sized to cover at least portion of the top 8a of the mattress 4. The cover includes a placket, which may be configured as a hem that partially secures the upper layer, lower layer and cushioning members together.

Continuing with FIGS. 5A and 5B, the upper and lower layers 354 and 358 can be formed from one or more textile materials. The textile materials that form the upper and lower layers can be woven, knit, or nonwoven fabrics. As needed, additional films or barriers may be included in the upper and/or lower layers. The textile materials for the textile article 310 may be a woven fabric, such as a plain weave, satin/sateen, twill, basket weave, or any other suitable woven construction. Woven fabrics can include synthetic warp and weft yarns, natural or blended warp and weft yarns, synthetic warp yarns with natural and/or blended weft yarns, natural warp yarns with synthetic weft yarns. The textile material may also include a knit fabric. The knit fabric may be a weft knit, such as single jersey knit fabric, a double knit, rib knit, or any other type of weft knitted fabric. The knit fabric may alternatively be a warp knit, such as a tricot or Rachel warp knitted fabric.

Continuing with FIGS. 5A and 5B, woven or knit textile materials forming the upper and lower layers 354 and 358 can be formed from any number of yarn types, such a spun yarns or continuous filament yarns. Spun yarns may include natural fibers, synthetic fibers, or blends of natural and synthetic staple fibers. Natural fibers include cotton, wool or others. Synthetic fibers may include polyethylene terephthalate (PET), viscose rayon, acrylic, or other fiber types, such a flame resistance fibers as needed. Suitable thermoplastic synthetic staple fibers may be mono-component or bi-component type fibers. A variety of yarn spinning types can be used, such as ring spun, open end, air-jet, and the like. Spun yarns can therefore include spun cotton yarns and/or spun cotton and polyethylene terephthalate (PET) blended yarns. Continuous filaments yarns may include either or both mono-component or bicomponent filaments types. Continuous filament yarns can be polyethylene terephthalate, polyolefin, and/or polyamide 6, polyamide 6,6, polylactic acid filaments.

Referring still to FIGS. 5A and 5B, the textile material for cover 301 may also be a nonwoven fabric. Suitable nonwoven fabrics include melt-spun nonwovens, such as spunbond and meltblown materials. A meltspun nonwoven can include a single spunbond layer, multiple spunbond layers, a single meltblown layer, multiple meltblown layers, or multiple layers of spunbond and meltblown materials. Meltspun nonwovens can from with polyethylene terephthalate, polyolefin, and/or polyamide 6, polyamide 6,6, or polylactic acid polymers. Alternatively, the nonwoven fabrics can be carded or airlaid materials that are bonded thermally, chemically, and/or mechanically, e.g. via needles or stitch bonding. Suitable fibers are carded or airlaid materials include PET and viscose fibers, and the like.

Referring to FIGS. 5A and 5B, the textile materials forming the upper and lower layers 354 and 358 can be formed from one or more layers of textile materials that include a number of functional finishes, coatings, or other treatments that enhance functionality of the cover 301. For instance, the upper layer can include anti-bacterial agents, coatings, flame retardant coatings, and the like. Furthermore, the textile materials may include barriers, such as films or other materials that can help inhibit penetration of particles through the cover into to the mattress.

Continuing with FIGS. 5A and 5B, the textile material forming the upper layer 354 can be formed from either one of a woven, knit, or nonwoven fabric. Furthermore, one or more woven, knit, and nonwoven fabrics can define the upper layer. For instance, the upper layer 354 can include multiple woven fabric layers configured as a laminate. Alternatively, the upper layer 354 can be a laminate of a woven and nonwoven fabric, a knit and nonwoven fabric, or even a woven and knit fabric. Likewise, the textile material forming the lower layer 358 can be formed from either one of a woven, knit, or nonwoven fabric. Furthermore, one or more woven, knit, and nonwoven fabrics can define the lower layer. In one example, the lower layer can include multiple woven fabric layers configured as a laminate. The lower layer could also be laminate of a woven and nonwoven fabric, a knit and nonwoven fabric, or even a woven and knit fabric.

Continuing with FIGS. 5A and 5B, the cushioning member 356 is configured to add loft and cushion to the cover. In one example, the cushioning member is a fibrous batting disposed between the upper and lower layers. For instance, the cushioning member can be an assembly of cut fibers arranged to provide loft and compression resilience to the cover 301. Any suitable fiber type can be used. In one example, polyester fibers are used as the fibrous batting. The fibrous batting can be loosely arranged without any specific bonding structure securing the fibers together. Alternatively, the fibrous batting can be air-laid nonwoven materials with either an adhesive or hot-melt bonding mechanisms used to provide structural integrity. In an alternative embodiment, the cushioning member can be a closed cell or open cell foam, such as natural or synthetic latex, or other foam types. In still other embodiments, the cushioning member can be down, such as a combination of down feather and other feathers. The cover 301 is quilted so as to secure the upper layer 354 to the lower layer 358.

A textile article can be configured as an absorbent article, such as an absorbent pad, wound dressing, bandage, or other medical textile used in a hospital or medical care setting. The absorbent article illustrated in FIGS. 6A and 6B is a wound dressing 640. However, the absorbent articles could be any absorbent pad designed to absorb bodily fluids.

As shown in FIGS. 6A and 6B, the wound dressing 640 is adapted for covering a wound of a patient. The wound dressing 610 includes at least one flexible sensor 140 integrated into or on the textile material 601. The flexible sensor 140 is configured to obtain sensor data that is indicative of the liquid in the textile material 601 that is in contact with the at least one flexible sensor 140. The wound dressing 610 further includes an interface element 150 that is electrically connected to the at least one flexible sensor 140. The interface element 150 is configured to forward the sensor data provided by the at least one flexible sensor to a computing device 120.

The flexible sensor 140 used in the wound dressing is substantially similar to the flexible sensor described above. For instance, each flexible sensor 140 has at least one first linear portion (not numbered) and at least one second linear portion (not numbered) that is spaced apart from the at least one first linear portion a distance D (D not shown in FIGS. 6A and 6B). As discussed above, the distance D can vary from 0.2 cm to about 5 cm. The flexible sensor 140 includes a conductive element, such as a yarn, laminate, inks, or design formed into the textile material as described above.

Continuing with FIGS. 6A and 6B, the wound dressing 610 includes the textile material 601 in the form of panel 620. The panel 620 has a first end 602, a second end 604 spaced from the first end 602 along a longitudinal direction L, and opposed side ends 606 and 608, respectively, spaced apart with respect to each other along a lateral direction A that is perpendicular to the longitudinal direction L. The panel 620 also includes a face 612 and a back 614 opposed to a face 612 along vertical direction V. The textile material 601 further includes at least one textile layer 622 that defines the face 612, and at least one absorbent component 624 disposed adjacent to the at least one textile layer 622. The absorbent component can absorb fluid from the wound of the patient when the wound dressing is applied to the wound. The absorbent component 624 defines the back 614 of the textile material 601 is typically placed directly adjacent the wound of the patient. In this way, the absorbent component 624 can absorb blood exuding from the wound as the wound heals.

The textile material 601 includes at least one textile layer 622. For example, the textile material 601 can include one textile layer 622 or a laminate of a plurality of textile layers 622. Each textile layer 622 can be a woven fabric, a knitted fabric, a nonwoven fabric, or any combination thereof. Furthermore, the textile layer 622 can include elastic components to provide stretch and recovery properties that aid in maintain the wound dressing 610 in place when applied to the patient. The absorbent component 624 can a textile fabric, such as a woven, knit, and/or a nonwoven material, that is formed for use on a wound of patient. Typically, the absorbent component may include absorbent materials and/or absorbent fibers that aid in absorbing fluids. For example, the absorbent materials include superabsorbent gels. The absorbent fibers include cotton, rayon, wool, or other fibers. In one example, the absorbent component is a gauze material made of cotton yarns. The textile material 601, whatever its construction, is formed from materials that are adapted for medical uses. For example, the materials may be manufactured in clean or controlled environments to minimize contamination. In some case, such materials may be irradiated to minimize bacterial growth The flexible sensors 140 are used to determine if an excessive amount of blood is exiting the wound. For example, if the absorbent component has been fully wetted out with blood and has absorbed its maximum capacity of fluid, the fluid will migrate through the textile layer 622. For instance, the flexible sensors 140 can detect the presence of fluid as described herein once the absorbent component is wetted out.

Figure 7:
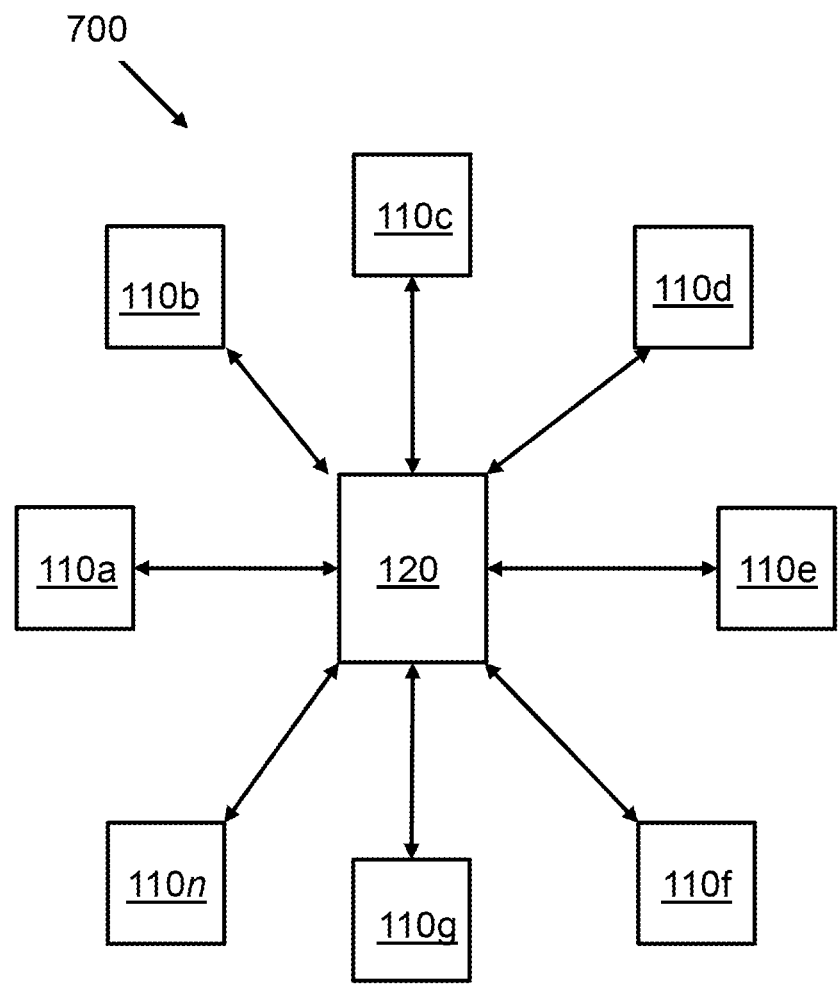
FIG. 7 is a block schematic diagram of a system for detecting liquid and/or other fluids according to another embodiment of the present disclosure.

FIG. 1A illustrates a system 700 that includes a computing device 120 and a plurality of textile articles 110. In accordance with the embodiment illustrated in FIG. 7, the plurality of textile articles 110a, 110b, 110b, . . . 110n are in electronic communication with the computing device 120. As shown in FIG. 7, each textile article 110a-110n includes a flexible sensor and an interface element 150 that is adapted to forward sensor data the computing device 120. The computing device 120, may, in turn, determine which textile article 110a through 110n includes moisture in contact with the flexible sensor 140 as described herein. In the embodiment shown in FIG. 7, the computing device 120 includes at least one software application configured for execution by a computer processor that is in electronic communication with the interface element of each of the plurality of textile articles 110a-110n. The software application is configured to, in response to receiving sensor data from the plurality of textile articles 110a-110n, a) determine if the sensor data indicates that a criterion is met for one or more of the plurality of textile articles 110a-110n, and b) based on the determination that the criterion is met for the one or more of the plurality of textile articles 110a-110n, determine if a respective one of the at least one flexible sensors is in contact with liquid. In the system 700 shown in FIG. 7, the textile articles can be a bedding article and/or a wound dressing as described herein.

In one example, the system 700 illustrated in FIG. 7 is suitable for healthcare applications, such a hospital or a nursing home facility. Such a system allows the central monitoring of moisture in multiple beds within a healthcare facility. For instance, if bodily fluids from a patient contact the flexible sensors 140, the computing device 120 initiates an alert at a terminal that prompts a healthcare provider to investigate further. Instances where bodily fluids may soak into bed clothing and contact sensors may include: bleeding, urination, or accidental removal of a wound dressing that causes bleeding.

Figure 8:
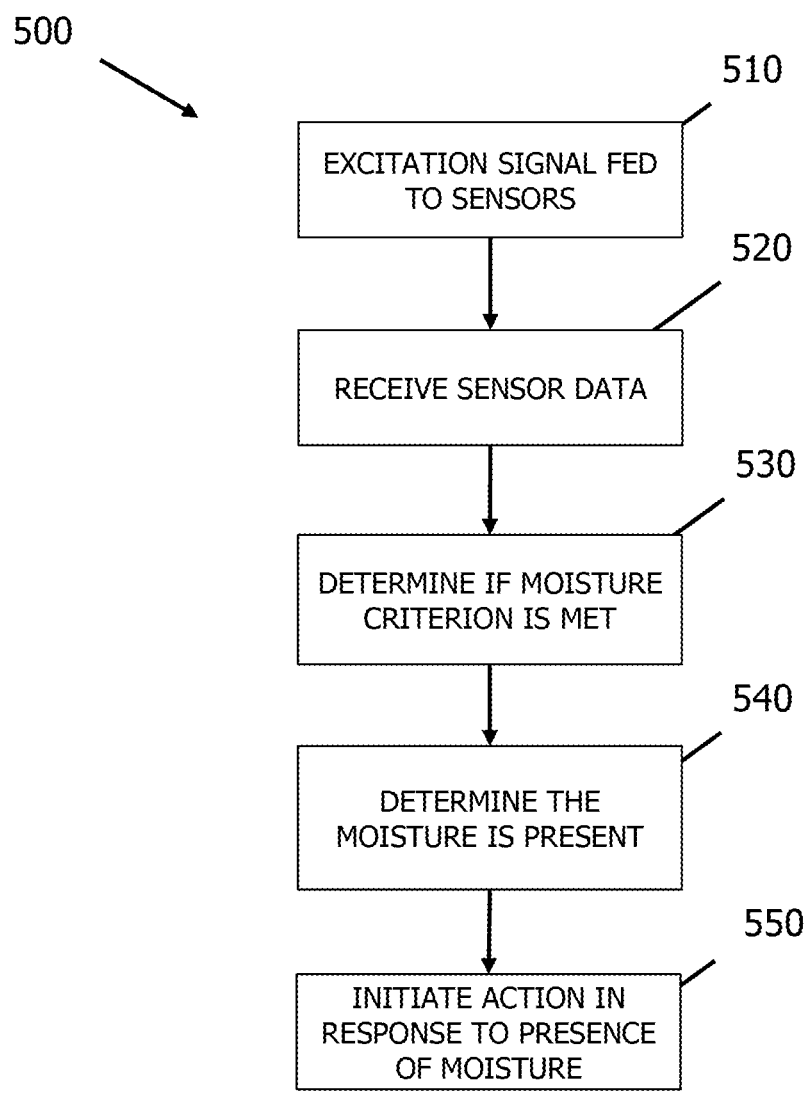
FIG. 8 is a flowchart illustrating a method for detecting liquid with a textile article.

FIG. 8 is a flowchart illustrating an embodiment of a method 500 for detecting liquid in a textile article as described herein. Method 500 may be performed by a computing device 120 that is communicatively coupled to the interface element 150 via a communication link 130. Initially, a liquid is released on the textile article. Through capillary action the liquid travels to the flexible sensor 140 in contact with both the first and second linear portions 146 and 148 of the flexible sensor 140. The liquid should span the distance D (see FIG. 2A). The liquid is conductive when in contact both the first and second linear portions 146 and 148 of conductive element 144 of the flexible sensor 140. In accordance with the illustrated embodiment, method 500 may comprise a step 510 whereby an excitation signal is fed to the one or more flexible sensors 140 via an interface element 150 of the textile article. The excitation signal is fed to the one or more flexible sensors 140 in response to an instruction communicated to the interface element 150 from the computing device 120 in a downlink direction 132 (FIG. 1A). Alternatively, the excitation signal is fed to the one or more flexible sensors in response to an instruction issued by the electronic component within the interface element 150.

At step 520, the computing device 130 receives sensor data associated with the sensor. At step 530, the computing device 120, via a software application executed by a processor, determines that a criterion is met based on the received sensor data. In an embodiment, the criterion may include any aspect of the criterion embodiments discussed above. For example, a criterion may be based on an electrical property associated with the one or more flexible sensors. As another example, a criterion may be based on a comparison between electrical properties corresponding to two or more flexible sensors 140 integrated into the textile article. In embodiments utilizing excitation signals, a criterion may be based on properties of the excitation signals. For example, the criterion may be based on a propagation time of an excitation signal through one or more of the textile sensors. As another example, the criterion may be based on a phase of an excitation signal after propagating through one or more of the textile sensors. In yet another example, the criterion may be based on a power level associated with an excitation signal after propagating through one or more of the textile sensors.

At step 540, the computing device 120, via the software application executed by the processor, determines that the textile material in a location proximate the one or more flexible sensors 140 is in contact with liquid. The determination in step 540 is based on the determination from step 530 that the criterion is met. At step 550, the computing device 120 initiates an action in response to determining that the textile material in a location proximate the one or more flexible sensors 140 is in contact with liquid. For example, the action may include the step of initiating an alert when the criterion is met. The method may also include the step storing in a computer memory occurrences that the criterion is met. Furthermore, the method may include the step of identifying a pattern among the occurrences that the criterion is met. The pattern can be a range of times that the one or more flexible sensors are likely to be in contact with liquid. The method can also include a step of determining the probability that the criterion will be met within a range of times (e.g. the processor is configured to determine that the sensor will likely be in contact with liquid between 9:30 pm and 10:30 pm). Furthermore, the method can include a step of determining when, over a range of times, the one or more flexible sensors 140 will likely be in contact with liquid. In response, the method can include initiating an alert previous to one of the identified range of times that the one or more flexible sensors will likely be in contact with liquid.

In method 500 described above, the sensor data may be transmitted by one textile article as in FIG. 1A. However, in alternative embodiment, the computing device receives sensor data from a plurality of textile articles 110a-110n as shown in FIG. 6. In such an embodiment where a plurality of textile articles 110a-110n are communicatively coupled to a computing device 120, step 520 may include determining which one of the plurality of the textile articles 110a-110n has moisture in contact with respective at least one flexible sensor. In such an embodiment, for instance, at step 550, the computing device 120 initiates an action in response to determining that the textile material in a location proximate the one or more flexible sensors 140 is in contact with liquid.

The present disclosure describes particular embodiments and their detailed construction and operation. The embodiments described herein are set forth by way of illustration only and not limitation. Those skilled in the art will recognize, in light of the teachings herein, that there may be a range of equivalents to the exemplary embodiments described herein. Most notably, other embodiments are possible, variations can be made to the embodiments described herein, and there may be equivalents to the components, parts, or steps that make up the described embodiments. For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

The techniques described above may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

As previously noted, the various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The present disclosure describes particular embodiments and their detailed construction and operation. The embodiments described herein are set forth by way of illustration only and not limitation. Those skilled in the art will recognize, in light of the teachings herein, that there may be a range of equivalents to the exemplary embodiments described herein. Most notably, other embodiments are possible, variations can be made to the embodiments described herein, and there may be equivalents to the components, parts, or steps that make up the described embodiments. For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

What is claimed is:

1. A system configured to detect liquid, the system comprising:
    a textile article having:
    a textile material having a top layer, an intermediate layer, and a bottom layer, wherein the intermediate layer includes a barrier component;
    at least one flexible sensor that obtains sensor data that is indicative of liquid in the textile material that is in contact with the at least one flexible sensor, the at least one flexible sensor including a conductive element, wherein an entirety of the conductive element is integrated into the top layer of the textile material; and
    an interface element that is electrically connected to the at least one flexible sensor, wherein the interface element is configured to forward the sensor data provided by the at least one flexible sensor to a computing device.

2. The system of claim 1, wherein the conductive element is a conductive yarn.

3. The system of claim 2, wherein the conductive yarn includes conductive fibers.

4. The system of claim 3, wherein the conductive fibers are stainless steel fibers.

5. The system of claim 2, wherein the conductive yarn forms a portion of the structure of the textile material.

6. The system of claim 2, wherein the conductive yarn is embroidered into the textile material.

7. The system of claim 1, wherein the textile material includes an absorbent layer and a barrier layer adjacent to the absorbent layer.

8. The system of claim 1, further comprising a power and data connector, wherein the interface element includes a connector having a plurality of contacts, wherein a first contact of the plurality of contacts is configured for power transmission and a second contact of the plurality of contacts is configured for data transmission, wherein the power and data connector includes a plurality of contacts that are configured to engage the plurality of contacts of the interface element.

9. A method for detecting liquid in at least one textile article, the method comprising:
    receiving sensor data associated with at least one flexible sensor an entirety of which is integrated into a top layer of a panel of the at least one textile article, wherein the panel includes the top layer, an intermediate layer, and a bottom layer, and the intermediate layer includes a barrier component, wherein the sensor data is indicative of liquid in the at least one textile article in contact with the at least one flexible sensor;
    based on the sensor data, determining with at least one computer processor of a computing device that a criterion is met; and
    based on the determination that the criterion is met, determining with the at least one processor that the at least one flexible sensor is in contact with liquid.

10. The method of claim 9, wherein the criterion is based on an electrical property associated with the at least one flexible sensor.

11. The method of claim 10, wherein the electrical property is one of: a resistance, a voltage, a resonant frequency, a reactance.

12. The method of claim 9, further comprising:
feeding an excitation signal to the at least one flexible sensor via an interface element disposed along the panel.

13. The method of claim 12, further comprising:
initiating an alert when the criterion is met; and
identifying a pattern among the occurrences that the criterion is met, wherein the pattern is a range of times that the at least one flexible sensor is likely to be in contact with liquid.

14. The method of claim 13, further comprising:
determining the probability that the criterion will be met within the range of times.

15. The method of claim 13, further comprising:
initiating an alert previous to one of the range of times that the at least one flexible sensor will likely be in contact with liquid.

\* \* \* \* \*